United States Patent
McGovern et al.

(10) Patent No.: US 10,351,542 B2
(45) Date of Patent: *Jul. 16, 2019

(54) EPOXIDATION PROCESS

(71) Applicant: Scientific Design Company, Inc., Little Ferry, NJ (US)

(72) Inventors: Shaun McGovern, Hoboken, NJ (US); Mansoor Husain, North Brunswick, NJ (US); John Sullivan, Wayne, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/672,945

(22) Filed: Aug. 9, 2017

(65) Prior Publication Data

US 2018/0044309 A1 Feb. 15, 2018

Related U.S. Application Data

(60) Provisional application No. 62/372,653, filed on Aug. 9, 2016.

(51) Int. Cl.
| | | |
|---|---|---|
| *C07D 301/10* | (2006.01) | |
| *B01J 8/06* | (2006.01) | |
| *C07C 7/12* | (2006.01) | |
| *C07D 301/32* | (2006.01) | |

(52) U.S. Cl.
CPC ............. *C07D 301/10* (2013.01); *B01J 8/06* (2013.01); *C07C 7/12* (2013.01); *C07D 301/32* (2013.01); *B01D 2259/402* (2013.01)

(58) Field of Classification Search
CPC .................................................. C07D 301/10
USPC ........................................................ 549/534
See application file for complete search history.

(56) References Cited

U.S. PATENT DOCUMENTS

| | | | |
|---|---|---|---|
| 3,563,914 A | 2/1971 | Wattimena | |
| 3,702,259 A | 11/1972 | Nielsen | |
| 3,844,981 A * | 10/1974 | Cusumano | B01J 23/48 502/324 |
| 4,376,209 A | 3/1983 | Watanabe et al. | |
| 4,761,394 A | 8/1988 | Lauritzen | |
| 4,766,105 A | 8/1988 | Lauritzen | |
| 4,822,926 A | 4/1989 | Dye | |
| 4,908,343 A | 3/1990 | Bhasin | |
| 5,011,807 A | 4/1991 | Hayden et al. | |
| 5,057,481 A | 10/1991 | Bhasin | |
| 5,099,041 A | 3/1992 | Hayden et al. | |
| 5,102,848 A | 4/1992 | Soo et al. | |
| 5,187,140 A | 2/1993 | Thorsteinson et al. | |
| 5,407,888 A | 4/1995 | Herzog et al. | |
| 6,242,655 B1 * | 6/2001 | Husain | C07C 29/76 568/852 |
| 7,294,317 B2 | 11/2007 | Billig et al. | |
| 9,096,561 B2 * | 8/2015 | Husain | C07D 301/06 |
| 2006/0189833 A1 | 8/2006 | Powell et al. | |
| 2007/0037991 A1 | 2/2007 | Rizkalla | |
| 2014/0309442 A1 * | 10/2014 | Husain | C07D 301/06 549/532 |
| 2016/0052899 A1 | 2/2016 | Iguichi et al. | |

FOREIGN PATENT DOCUMENTS

KR 1020070070454 A 7/2007

OTHER PUBLICATIONS

Bhattacharyya, Feb. 2012, John Wiley Applications of Ion Chromatography.*
International Search Report dated Nov. 20, 2017, received in a corresponding foreign application.

* cited by examiner

*Primary Examiner* — Nizal S Chandrakumar
(74) *Attorney, Agent, or Firm* — Scully Scott Murphy and Presser

(57) ABSTRACT

A method for the oxidation of ethylene to form ethylene oxide which comprises: providing an aqueous stream containing ethylene glycol and impurities; introducing the aqueous stream in a first ion exchange treatment bed to reduce the content of these impurities; determining whether an outlet of the first ion exchange treatment bed has a conductivity greater than about 5 μS/cm; upon determining that the outlet of the first ion exchange treatment bed has a conductivity greater than about 5 μS/cm, introducing the outlet of the first ion exchange treatment bed into a second ion exchange treatment bed; and upon determining that the outlet of the first ion exchange treatment bed has a conductivity greater than about 60 μS/cm, redirecting the introduction of the aqueous stream to the second ion exchange treatment bed and regenerating the first ion exchange bed.

8 Claims, 7 Drawing Sheets

PRIOR ART

EPOXIDATION PROCESS

CROSS REFERENCE TO RELATED APPLICATION

The present invention claims the benefit of U.S. Provisional Patent Application No. 62/372,653 filed Aug. 9, 2016, the entire content and disclosure of which is incorporated herein by reference.

FIELD OF THE INVENTION

The present invention relates to a method for the oxidation of ethylene into ethylene oxide.

BACKGROUND OF THE INVENTION

Though present in natural settings at minute quantities, ethylene oxide was first synthesized in a laboratory setting in 1859 by French chemist Charles-Adolphe Wurtz using the so-called "chlorohydrin" process. However, the usefulness of ethylene oxide as an industrial chemical was not fully understood in Wurtz's time; and so industrial production of ethylene oxide using the chlorohydrin process did not begin until the eve of the First World War due at least in part to the rapid increase in demand for ethylene glycol (of which ethylene oxide is an intermediate) as an antifreeze for use in the rapidly growing automobile market. Even then, the chlorohydrin process produced ethylene oxide in relatively small quantities and was highly uneconomical.

The chlorohydrin process was eventually supplanted by another process, the direct catalytic oxidation of ethylene with oxygen, the result of a second breakthrough in ethylene oxide synthesis, discovered in 1931 by another French chemist Thèodore Lefort. Lefort used a solid silver catalyst with a gas phase feed that included ethylene and utilized air as a source of oxygen.

In the eighty years since the development of the direct oxidation method, the production of ethylene oxide has increased so significantly that today it is one of the largest volume products of the chemicals industry, accounting, by some estimates, for as much as half of the total value of organic chemicals produced by heterogeneous oxidation. Worldwide production in the year 2000 was about 15 billion tons. (About two thirds of the ethylene oxide produced is further processed into ethylene glycol, while about ten percent of manufactured ethylene oxide is used directly in applications such as vapor sterilization.)

The growth in the production of ethylene oxide has been accompanied by continued intensive research on ethylene oxide catalysis and processing, which remains a subject of fascination for researchers in both industry and academia. Of particular interest in recent years has been the proper operating and processing parameters for the production of ethylene oxide using so-called "high selectivity catalysts", that is, Ag-based epoxidation catalysts that are especially efficient at catalyzing the desired product reaction of ethylene and oxygen to ethylene oxide rather than the side reaction of ethylene and oxygen, which produces carbon dioxide byproduct (and water).

However, while high selectivity catalysts have reduced the formation of carbon dioxide byproduct, they may also have increased the production of other undesired byproducts, notably aldehydic impurities such as acetaldehydes and formaldehydes and their associated acids as well as dissociated ions. Acetaldehyde and formaldehyde have long been known as byproducts formed during the operation of ethylene oxide plants. Acetaldehyde is formed as a result of the isomerization of ethylene oxide, while formaldehyde is formed by the reaction of ethylene oxide with oxygen. The associated acids, acetic acid and formic acid, are produced by oxidizing acetaldehyde and formaldehyde, respectively. The presence of aldehydes and their associated acids can negatively affect the UV quality of the ethylene glycol solution and thereby cause degradation of the fiber grade ethylene glycol product. Additionally, the formation of their associated acids (as well as their aldehydic reagents) can decrease the pH to levels sufficiently low to cause corrosion in the plant. These considerations are even more serious in plants that produce fiber grade ethylene glycol. It is additionally important to note that while an impurity like carbon dioxide is produced almost exclusively on the catalyst bed in the EO reactor, acetaldehydes, formaldehydes and their associated acids are produced both on the catalyst and past the catalyst bed.

One possible method of preventing or reducing the corrosion caused by acidic pH levels is to replace the carbon steel components with stainless steel components. While this is highly effective in at least reducing the rate of corrosion if not completely preventing it, using stainless steel components adds some expense and generally cannot be retrofitted into an existing plant. Moreover, this of course does not address the problem of low ethylene glycol product quality resulting from contamination by impurities.

Another possible solution is disclosed in U.S. Pat. No. 4,822,926 in which the reactor product stream is supplied to a quench section (the quench section being disposed inside the EO absorber), and in the quench section the reactor product stream is contacted with a base-containing recirculating aqueous solution in order to neutralize the pH and eliminate some of the organics. The addition of a base, like e.g., sodium hydroxide, does increase the pH (and as a consequence reduces the corrosion in the plant) as well as prevent the formation of some of the organics and aldehydic impurities. But the addition of caustic also frequently causes the decomposition and degradation of the ethylene glycol product, especially for heavier ethylene glycols like triethylene glycol, which often cannot be manufactured to meet minimum quality standards in a process utilizing caustic. Thus, in the end, caustic addition merely exchanges one problem (corrosion and impurity formation) for another (poor product quality).

Other technologies have also been developed in an attempt to reduce the formation of acetaldehyde and formaldehyde and associated impurities. For example, it has long been known that the isomerization of ethylene oxide to various aldehyde species occurs more readily at higher temperatures. This problem can be particularly pronounced as the product effluent leaves the reactor outlet at high temperatures and is largely maintained at such temperatures until entering a heat exchanger in order to cool the gas prior to its delivery to the absorption section.

Thus, techniques and equipment designs have been developed to reduce the temperature of the ethylene-containing product gas as quickly as possible. U.S. Pat. No. 4,376,209 discloses the use of inerts in a cooling zone of the reactor to cool the gas, however, as the patent makes clear, this technique produced mixed results, and possibly actually increases acetaldehyde make as much as suppressing its formation.

Another approach is the integrated reactor-cooler assembly disclosed in U.S. Pat. No. 7,294,317, which is designed to bring about a sharp drop in the temperature of the ethylene-containing gas. However, while the integrated reactor-cooler has shown itself to be extremely successful at reducing the formation of byproducts, it fails to address those impurities that are generated at later processing stages. However, an extensive retrofit and revamp is necessary in order to accommodate the reactor-cooler assembly described in the aforementioned patent.

The use of ion exchange resins requires less reworking for already-existing plants than the integrated reactor-cooler assembly and are highly efficacious at eliminating aldehydic and other impurities from the cycle water. Suitable ion exchange resins are such as those disclosed in U.S. Pat. No. 6,187,973. These ion exchange resins are extremely effective at removing the impurities from the cycle water, without causing the negative consequences mentioned above from caustic treatment. Nonetheless, while ion exchange resins provide excellent performance in removing impurities, difficulties with their use remain. For example, ion exchange resins require frequent regeneration to restore the ability of the resin to capture and adsorb ions and impurities. These regeneration cycles, have to be repeated more frequently as the quantity of byproducts increases. These regeneration cycles considerably complicate the operation of the ethylene oxide process and reduce its efficiency because they require that the spent or exhausted ion exchange bed must be removed from service and a standby bed on-line in its place. This increasing frequency in the regeneration cycle is undesirable because each such cycle requires considerable amounts of demineralized water, and regeneration chemicals; and simultaneously generating waste water that requires treatment and disposal. Given the costs of supplying the demineralized water and chemical, and the costs of treating and disposing of the waste water, there is thus an imperative to reduce the frequency of the regeneration cycles.

Given the foregoing there is a continuing need in the art for techniques to reduce the frequency of regenerating the ion exchange resins.

BRIEF SUMMARY OF THE INVENTION

The present invention relates to a method for the oxidation of ethylene to form ethylene oxide which comprises: providing an aqueous stream containing ethylene glycol and impurities; introducing the aqueous stream in a first ion exchange treatment bed to reduce the content of these impurities; determining whether an outlet of the first ion exchange treatment bed has a conductivity greater than about 5 µS/cm; upon determining that the outlet of the first ion exchange treatment bed has a conductivity greater than about 5 µS/cm, introducing the outlet of the first ion exchange treatment bed into a second ion exchange treatment bed; and upon determining that the outlet of the first ion exchange treatment bed has a conductivity of greater than about 20 µS/cm, preferably greater than about 100 µS/cm, redirecting the introduction of the aqueous stream to the second ion exchange treatment bed and regenerating the first ion exchange bed.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
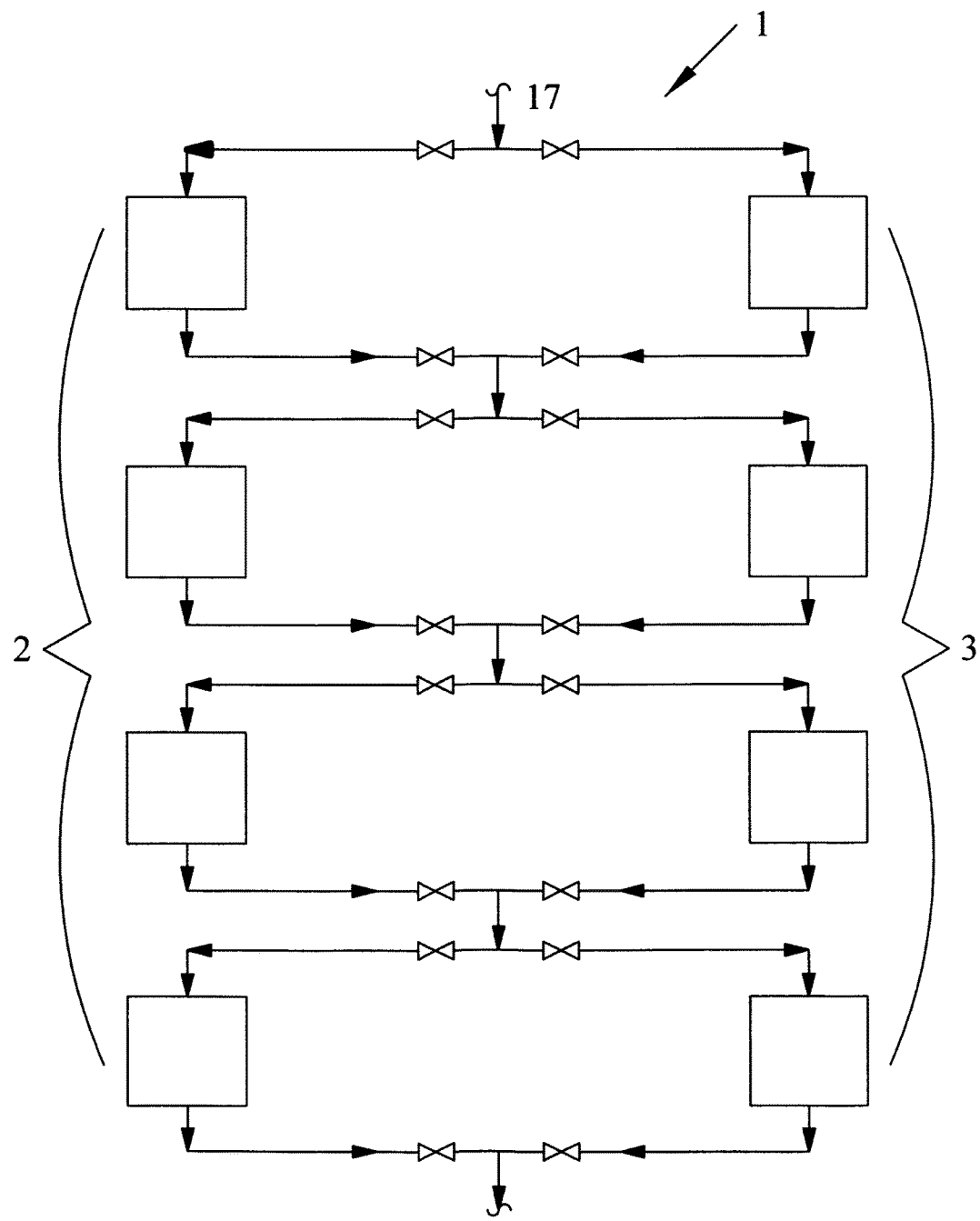
FIG. 1 is a schematic flow sheet showing two trains of ion exchange treatment beds configured according to the prior art.

All parts, percentages and ratios used herein are expressed by volume unless otherwise specified. All documents cited herein are incorporated by reference.

By "ion exchange resin" it is meant any conventional ion exchange resin, as known to a skilled person and, which is a readily-available article of commerce.

It has been found in the present invention that the frequency of regeneration cycles can be reduced and product quality improved by simultaneously operating first and second ion exchange treatment beds. In conventional, prior art operation, an ion exchange treatment bed was operated until "exhausted" (as described below), at which time it was bypassed and regenerated while a second ion exchange treatment bed put online in its place. The regenerated bed was left bypassed until subsequent exhaustion of the second bed.

By contrast, in the present invention the first and second ion exchange treatment beds are operated simultaneously. One embodiment of this involves the first and second ion exchange treatment beds in a "lead-lag" configuration. As soon as "breakthrough" (as described below) is observed in the outlet of the first ion exchange treatment bed (the "lead" bed) then the second ion exchange treatment bed (the "lag" bed) is also brought on-line (see FIG. 3, below) with impurity-containing solution being passed through both ion exchange treatment beds. Doing this greatly reduces the frequency of regeneration and thus, reduces the consumption of demineralized water, and regeneration chemicals, while generating less waste water.

Alternatively, the first ion exchange treatment bed and second ion exchange treatment bed can be operated simultaneously before breakthrough is observed in the outlet of the first ion exchange treatment bed. In this case, small leakages from the first ion exchange treatment bed that may occur even before breakthrough is observed will be captured by the second ion exchange treatment bed, while at the same time the capacity of the second ion exchange treatment bed will be largely reserved for use later in the service cycle after the first ion exchange treatment bed nears exhaustion.

In addition to the process efficiencies described above, the simultaneous use of a first and second ion exchange treatment beds result in an important effect. It has been determined in the present invention that maintaining the impurity levels in an aqueous stream (preferably this aqueous stream is a bleed stream from the lean cycle water) below an impurity concentration as measured by a conductivity of less than 5 µS/cm results in superior product quality and reduces impairment to plant equipment that may be degraded by, for example, corrosion caused by high impurity levels in the aqueous stream.

The use of this invention will now be described below in greater detail, below, as a component of an ethylene oxide production process.

Ethylene oxide is produced by continuously contacting an oxygen-containing gas with an olefin, preferably ethylene, in the presence of an ethylene oxide ("epoxidation") catalyst (described in greater detail below). Oxygen may be supplied to the reaction in substantially pure molecular form or in a mixture such as air. By way of example, typical reactant feed mixtures under operating conditions may contain from about 0.5% to about 45%, preferably about 5% to about 30% of ethylene and from about 3% to about 15% oxygen, with the balance comprising comparatively inert materials including such substances as carbon dioxide, water, inert gases, other hydrocarbons, and the reaction moderators described herein. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum.

Also present in the reaction, as previously mentioned, are one or more reaction moderators, non-limiting examples of which include organic halogen-containing compounds such as $C_1$ to $C_8$ halohydrocarbons; especially preferred are chloride-containing moderators such as methyl chloride, ethyl chloride, ethylene dichloride, vinyl chloride or mixtures thereof. Controlling chloride concentration level is particularly important with rhenium-containing catalysts.

As mentioned above, a usual method for the ethylene epoxidation process comprises the vapor-phase oxidation of ethylene with molecular oxygen, in the presence of an epoxidation catalyst, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-53 feet long, each filled and packed with catalyst. The reaction feed mixture (described above) is introduced into these tubes, and the resulting reactor effluent gas contains ethylene oxide, un-used reactants, and byproducts.

For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production rate (work rate) of 7-20 lbs. EO/cu.ft. catalyst/hr. The feed composition in the reactor inlet after the completion of start-up and during normal operation typically comprises (by volume %) 1-40% ethylene, 3-12% $O_2$; 0.3% to 20%, preferably 0.3 to 5%, more preferably 0.3 to 1% of $CO_2$; 0-3% ethane, an amount of one or more chloride moderators, which are described herein; and the balance of the feed being comprised of argon, methane, nitrogen or mixtures thereof.

Typical operating conditions for the ethylene epoxidation process involve temperatures in the range from about 180° C. to about 330° C., and preferably, from about 200° C. to about 325° C., and more preferably from about 225° C. to about 280° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 2 to about 20 seconds.

The reactor effluent exits through the reactor outlet, is cooled and flows to the EO scrubbing column, where the reactor effluent is contacted with recirculated lean cycle water to absorb the ethylene oxide from the reactor effluent. These scrubbing column liquids (rich cycle water) are then fed to the EO stripping column for the recovery of the ethylene oxide. In the EO stripping column, the ethylene oxide is stripped out and the ethylene oxide vapor is sent overhead to a second EO absorber. The liquid water flows through the stripping column bottoms (referred to herein as the "lean cycle water") and a bleed stream is taken from the lean cycle water before the lean cycle water is returned to the EO scrubber where it is used to absorb ethylene oxide. This bleed stream is an aqueous stream that comprises about 0.2 to 20 wt % ethylene glycol, about 80 to 99.7 wt % water and about 100 ppm to 1.0 wt % impurities. Impurities can include, inter alia, aldehydic impurities such as formaldehyde, acetaldehyde, glycolaldehyde, their associated acids and ions, as well as their reaction products such as long-chain esters that are produced as a result of the reaction of aldehydic impurities with ethylene oxide and/or ethylene glycol. This aqueous stream is then sent to a lean cycle water treatment unit. FIG. 1 shows a prior art lean cycle water unit 1 containing two trains 2, 3, each train containing multiple ion exchange treatment beds (represented as boxes in FIG. 1) arranged in series for treating an aqueous stream 17 taken as a bleed stream as described above. Each ion exchange bed is selected from either an anion or cation ion exchange bed, or possibly instead substituted with another adsorbent bed of another material as described elsewhere herein. In the prior art process of FIG. 1, the ion exchange beds are operated strictly as a train rather than individually. Thus, while all of the ion exchange beds of one train are in active operation, the other beds are bypassed and are either being regenerated or wait inactively in standby mode.

Figure 2:
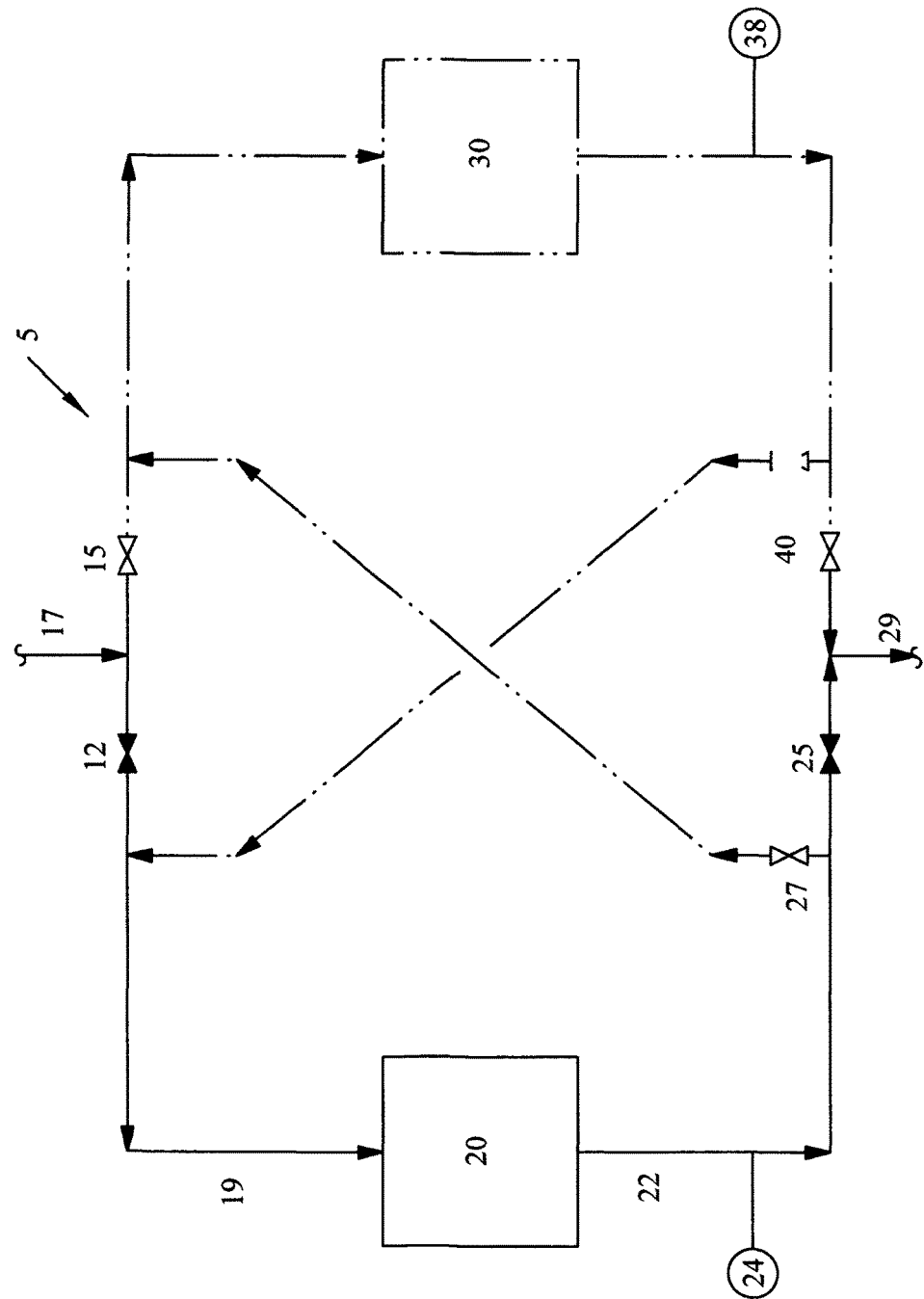
FIG. 2 is a schematic flow sheet of an embodiment of a method for treating an aqueous stream with an ion exchange treatment bed.

FIG. 2 shows a treatment unit 5 constructed according to the present invention with two ion exchange treatments beds 20, 30. In FIG. 2, valve 12 is opened while valve 15 is closed so that the aqueous stream 17 containing ethylene glycol and the above-described impurities is sent through conduit 19 and introduced into a first ion exchange treatment bed 20 where the aqueous stream is contacted with ion exchange resin to reduce the concentration of the impurities. The aqueous stream is contacted with this ion exchange resin at temperatures of from about 30° C. to about 50° C. although higher or lower temperatures may be used. Atmospheric pressure is preferred, but higher pressures can also be used depending on whether a pressure differential in the next processing unit is desired. Illustrative flow rates are about 1 to 10 volumes of solution per volume of resin per hour although this can vary widely. An analyzer 24 placed on the outlet 22 of the first ion exchange treatment bed 20 measures the conductivity, pH, or the UV transmittance of the aqueous stream 22 from the first ion exchange treatment bed to determine the approximate concentration of ions and impurities in the outlet 22. These techniques, which are discussed in greater detail below, are used to determine whether "breakthrough" of the impurities has occurred. Breakthrough occurs when many or most of the functional groups on the active sites on an ion exchange resin have been exchanged with target ions or impurities and thus, the ion exchange treatment bed no longer has sufficient capacity to absorb all of the impurities from the aqueous stream, leaving some measurable concentration of impurities to pass over the ion exchange resin "uncaptured" into the outlet stream. As some small concentration of impurities is always able to pass through the ion exchange treatment bed, in the present invention breakthrough is defined not at zero concentration of impurities or ions or zero measured conductivity, but rather breakthrough occurs when sufficient concentrations of impurities pass through the ion exchange treatment bed to result in conductivity measured in the aqueous stream to greater than 5 μS/cm.

FIG. 2 shows the case where such breakthrough has not occurred; in this case upon determining that the outlet of the first ion exchange treatment bed has a conductivity of less than about 5 μS/cm (alternatively, measurements of UV transmittance or pH can be used to determine if breakthrough has occurred); valve 25 remains open and valve 27 closed so that the aqueous stream passes through the outlet 22 from the first ion exchange treatment bed 20 flows as an exit stream 29 out of the treatment unit 5. (The dotted lines in the accompanying Figures show conduits, piping and ion exchange treatment units that are bypassed when one or more of the valves are closed to prevent fluid communication.) Once out of the treatment unit 5, the aqueous stream may be subjected to further treatment or processing or preferably sent to the ethylene glycol purification section of an ethylene oxide/ethylene glycol plant. For example, if the ion exchange treatments bed 20 treatment unit 5 contains cationic resin, the aqueous stream may then flow to a treatment unit containing anionic resins. If on the other hand the impurity level has been sufficiently reduced so that the aqueous stream may then be further processed without damaging the plant or the product quality, then this aqueous stream may be sent back to the plant, such as the ethylene glycol purification section of the plant. As shown in FIG. 2, the second ion exchange treatment bed is bypassed and disconnected from any circulating feed or streams and while being bypassed the second ion exchange treatment bed may simply be in standby mode ready for possible use, or alternatively may be in the process of being regenerated, having been exhausted by previous use.

Figure 3:
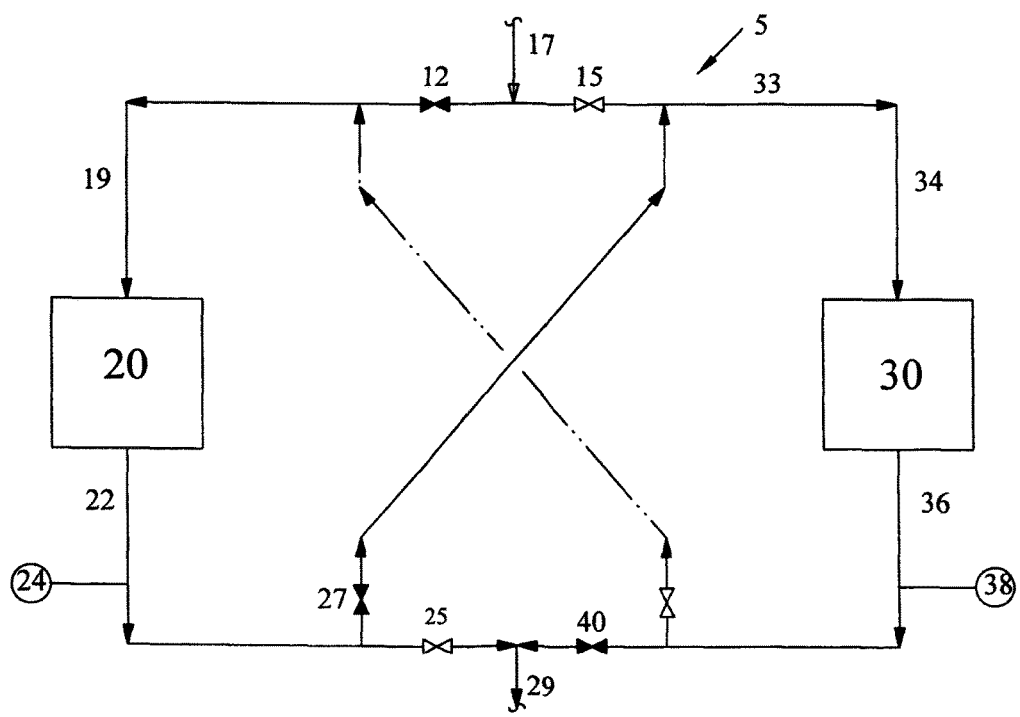
FIG. 3 is a schematic flow sheet of a further embodiment of a method for treating an aqueous stream with two ion exchange treatment beds.

In contrast to FIG. 2, FIG. 3 shows the configuration of the treatment unit 5 after conductivity in the outlet 22 is measured to be greater than about 5 μS/cm indicating that breakthrough has occurred. As breakthrough indicates that the first ion exchange treatment bed alone is no longer sufficient to reduce the concentration of ions and impurities to the desired levels, valve 25 is closed and valve 27 opened so that the aqueous stream passes through the first outlet stream 22 from the first ion exchange treatment bed flow through conduits 32-33 and is then introduced through an inlet stream 34 into a second ion exchange treatment bed 30, where it is contacted with an ion exchange resin to reduce the concentration of the impurities in the inlet stream to result in a treated stream 36. The pressure, temperature and flow rate at which the aqueous stream contacts the ion exchange resin in the second ion exchange treatment bed 20 are within the same ranges as set forth above for the first ion exchange treatment bed 30.

The treated stream is measured by a second analyzer 38, which like analyzer 24 may make measurements of UV transmittance, pH, conductivity, or any other suitable measurement for determining the concentration of the treated stream 36. The stream then flows through closed valve 40 and through the exit 29. After passing through exit 29, as described above, depending on the measured impurity level and the preferred order of ion exchange treatment, the stream may then flow to another treatment unit or may be returned to the plant.

As mentioned above, FIG. 3 shows the situation where breakthrough in the first ion exchange treatment bed 20 has occurred but the bed is not yet exhausted and in need of regeneration due to the availability of the second bed to capture impurities. When the measured conductivity (or equivalent pH or UV transmittance measurements) in either analyzer 24, 38 is greater than about 20 μS/cm, preferably greater than about 100 μS/cm (or alternatively when the percentage reduction in the measured conductivity is 30 to 70% measured relative to the initial measured conductivity), then the first ion exchange bed 20 has reached exhaustion and needs to be bypassed so it can be regenerated. This is shown in FIG. 4.

Figure 4:
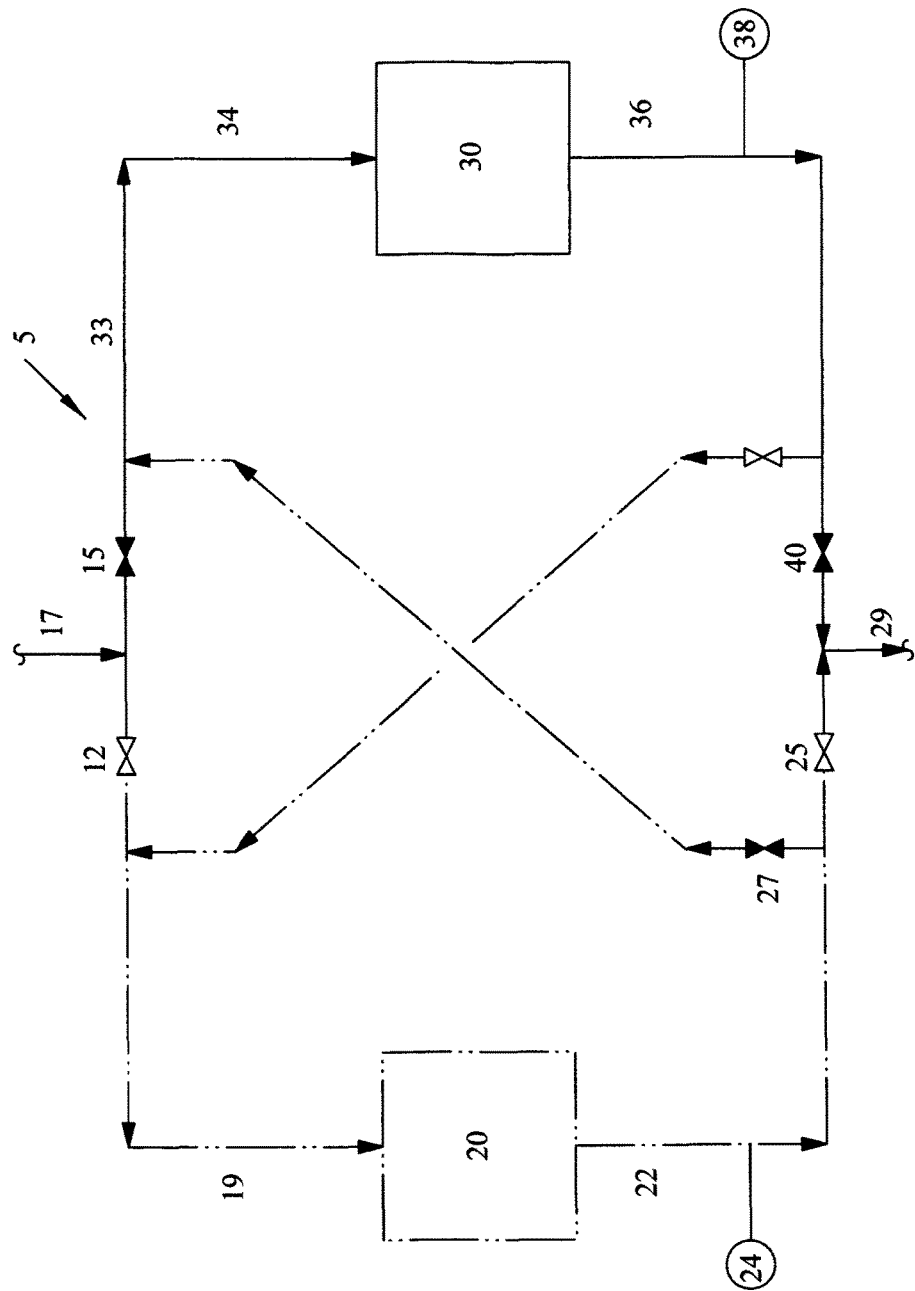
FIG. 4 is a schematic flow sheet of an embodiment of a method for treating an aqueous stream with one ion exchange treatment bed.

FIG. 4 represents essentially the mirror image of FIG. 2. In the treatment unit 5 of FIG. 4, valve 12 is closed and valve 15 opened so that the first ion exchange treatment bed 20 is bypassed and the aqueous stream flows in through 17, through inlet 32 and is then introduced in the second ion exchange bed 30 where it is contacted with an ion exchange resin to reduce the concentration of the impurities. The conductivity (or pH or UV transmittance) of the aqueous stream in the second ion exchange treatment bed's outlet 36 is then measured by the second analyzer 38 and provided that this measurement does not show breakthrough in the outlet stream is sent through closed valve 40 and through exit 29 for further treatment or further use in the ethylene oxide/ethylene glycol manufacturing process as described above.

While the first ion exchange treatment bed 20 is being bypassed in treatment unit 5 as shown in FIG. 4, it may simultaneously be regenerated or merely be positioned in standby mode.

FIG. 3, above, may also represent an alternate embodiment. In this embodiment the treatment unit is configured so that the aqueous stream passes through both the first and second ion exchange treatment beds 20, 30. (In addition to the two ion exchange treatment beds explicitly shown, one or more additional ion exchange treatment beds may also be used). In this case, ion exchange treatment bed 30 effectively acts as a polishing unit to capture small leakages of impurities from the first ion exchange treatment bed even prior to breakthrough of the first ion exchange treatment bed. In this configuration, valve 25 is closed and valve 27 opened so that the aqueous stream passes through the first outlet stream 22 from the first ion exchange treatment bed flow through conduits 32-33 and is then introduced through an inlet stream 34 into a second ion exchange treatment bed 30, where it is contacted with an ion exchange resin to reduce the concentration of the impurities in the inlet stream to result in a treated stream 36. The pressure, temperature and flow rate at which the aqueous stream contacts the ion exchange resin in the second ion exchange treatment bed 30 are within the same ranges as set forth above for the first ion exchange treatment bed 30. The use of the first and second ion exchange treatment beds together increases the time between regenerations because when the capacity of the first ion exchange treatment bed has been reached and the bed nears exhaustion, the second ion exchange treatment bed is still relatively "fresh" with ample capacity to absorb additional ions and impurities. When the measured conductivity exceeds about 5 μS/cm, the unit 5 can be taken off-line and regenerated.

As mentioned above, after the treated stream is passed out of the treatment unit through exit 29 after being treated in either the first ion exchange bed 20, the second ion exchange bed 30, or both, the stream may be treated further. In a preferred embodiment of the present invention, the first ion exchange bed 20 and the second ion exchange bed 30 are each part of separate trains of ion exchange treatment beds arranged in series configuration as shown fully in FIG. 5, which is prepared according to the present invention. As seen in this FIG. 5, there are multiple treatment units, 5, 6, 7, 8 for treating an aqueous stream 17 taken as a bleed stream as described above further consisting of additional ion exchange treatment beds 50, 55, 60, 65, 70, and 75 and their respective analyzers 51, 52, 61, 62, 71, and 72. After passing through the treatment units shown in FIG. 5, the stream finally exits through pipe 45 for further use in the ethylene oxide/ethylene glycol manufacturing process as described above.

Figure 5:
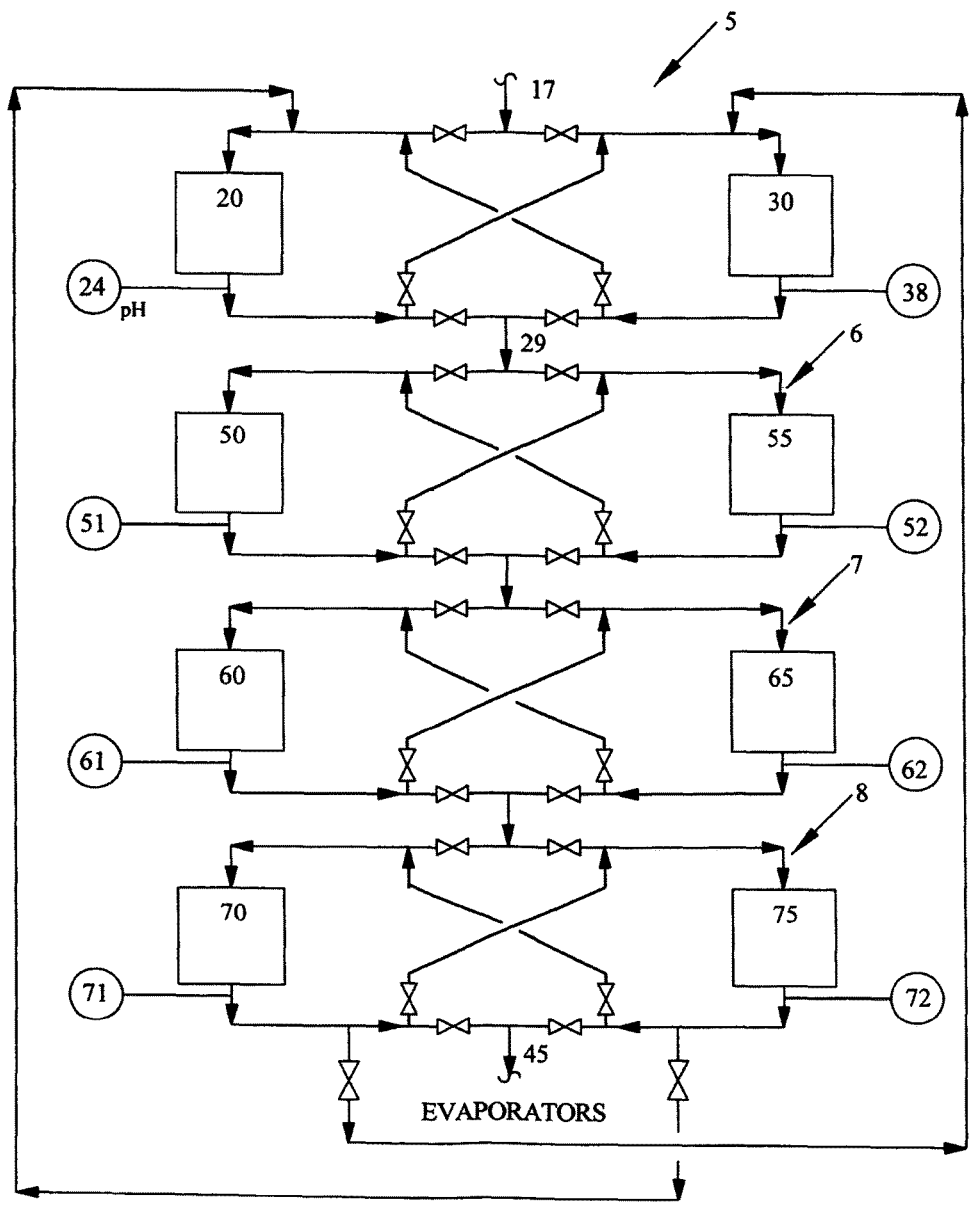
FIG. 5 is a schematic flow sheet showing two trains of ion exchange treatment beds configured according to the present invention allowing fluid communication between parallel ion exchange treatment beds.

In FIG. 5, it can be seen that the configuration of piping which allows fluid communication between the first and second ion exchange treatment beds, above, has been expanded to allow fluid communication between parallel ion exchange treatment beds. FIG. 5 shows how the configuration and interconnection of parallel two ion exchange beds can be expanded to interconnect two entirely separate trains. It should be noted that FIG. 5 does not show the unit in actual operation as no valves are opened or closed to direct the aqueous streams through select treatment beds.

Ion Exchange Resins

As discussed above, the present invention may involve one or more ion exchange treatment resins. Ion exchange resins have a polymer matrix which contain on the surface ion exchanging sites populated by ionic functional groups. Ion exchange resins are typically differentiated between cationic or anionic exchange resin, although other types of ion exchange resins are also available.

Suitable polymer matrices for the ion exchange bed include a polystyrene matrix, a polyacrylic matrix, a polyalkylamine resin as well as others polymeric materials. Preferably, the polymer matrix is cross-linked with divenylbenzene to a sufficient degree to increase the operating capacity while also not increasing the density of the ion exchange material to such an extent that the ion exchange material becomes too physically hard and too chemically resistant to chemical treatment. Preferably the matrix is a styrene, divenylbenzene co-polymer. In addition to the aforementioned structures, alternative materials and structures may also be used such as macroporous resins and natural ion exchange materials such as clay and zeolite minerals.

Disposed on the active sites of the ion exchange resin are ionic functional groups that determine whether the resin functions as a cationic or anionic ion exchange bed. Strongly acidic cationic ion exchange resins typically include sulfonic groups. Examples of strongly acidic sulfonic cation-exchange resins include Amberlite IR 120, Dowex HCR, Lewatit S 100, and Amberlyst 15, among others. Weakly acidic cationic ion exchange resins typically include carboxylic groups. Examples of weakly acidic cation-exchange resins include Amberlite IRC 86, and Lewatit CNP, among others. Further examples of suitable cation-exchangers include the Tulsion T56MP and TG 057 cation exchanger from Thermax LTD, Pune, India.

Suitable anion-exchange resins include chloromethylated polystyrene which can be made in a variety degrees of basicity and include various Amberlite grades such as IRA 402, IRA 410, and IRA 96. Weakly Anion exchange resins can also include polyacryclic resins provided with functional groups by reaction with a polyfunctional amine to result in an anion exchange resins such as the tertiary weakly basic Amberlite IRA 67 and Amberlyst A21 or then further treated with chloromethane or dimethyl suflate to give a quaternary amine strongly basic resin IRA 458.

Further examples of suitable anion exchange resins include, Tulsion A8X MP and A9X MP anion exchangers from Thermax LTD and those anion exchange resins disclosed in U.S. Pat. No. 6,187,973, herein incorporated by reference.

In addition to the specified ion exchange materials specified above, any other suitable cationic or anionic exchange resin may be used such as the cation- and anion-exchange resins set forth in de Dardel, F. and Arden, T. V. 2008, *Ion Exchanger*, in *Ullman's Encyclopedia of Industrial Chemistry*.

Ion Exchange Regeneration

As mentioned above, when not in use, the ion exchange treatment beds can either be in stand-by mode or undergoing regeneration in the event of exhaustion. Regeneration occurs by washing the solid adsorbent and ion exchange resin with a regenerant to remove and displace the impurities and ions adsorbed by the resin and replenish at the active sites on the resin the respective counter-ions released by the resin into the solution, thus restoring the ability of the resin to capture and adsorb ions and impurities. During regeneration, these impurities, ions and other organics elute and are released into the liquid regenerant. The regenerant should be specifically selected to replenish the ions on the surface of the ion exchange resin—for example sodium hydroxide regenerate is preferred for regenerating an anion bed with hydroxide functional groups in particular for replenishing the hydroxide that has been released by the resin during service. Similarly, for a cation resin with hydrogen ion functional groups, regeneration is typically accomplished by the use of HCl or sulfuric acid as the regenerant. Other typical regenerants include sodium sulfate.

Typically regeneration is followed by a rinsing cycle with demineralized water to displace the regenerant from the ion exchange bed. This rinsing may be accomplished in one or more cycles, with each cycle conducted under different parameters, like flow rate. At the completion of the rinsing step, the ion exchange bed should be free of regenerant.

In addition to the aforementioned ion exchange treatment beds, a vacuum degassifier (not shown) may be used to reduce the free carbon dioxide in a stream to levels of a few ppm.

Degasifier

The system may be designed with or without a vacuum degasifier depending on the preferences of the user. The degasifier functions by removing carbon dioxide from the aqueous stream. Because carbon dioxide is a relatively weak acid, by removing it from the aqueous stream, then a weak base may be used for removal of the remainder of the impurities instead of a strong base since carbon dioxide does not need to be removed from the aqueous stream. The use of a weak base resin rather than a strong base resin reduces the amount of chemicals needed for regeneration. Thus, the degasifier increases capital costs (the cost of the degasifier increases capital costs) while reducing operating costs (less chemicals for regeneration lowers the operating cost). Thus, the selection of which of these options is up to the individual end user.

Analyzer Units

Analyzers are placed in the various outlet streams to provide continuous online measurement of the performance of the ion exchange treatment beds in removing impurities. As mentioned above, any suitable analytical technique may be used in this application, including measurement of the conductivity, pH, or the UV transmittance of the outlet stream.

Conductivity can be used to measure the concentration of impurities in the stream because water, as a non-electrolyte, is generally a poor conductor. However, as a result of electrolytic dissociation, acids, bases and other impurities dissociate in the water into ions allowing determination of the electrolytic content of the water. Thus, strong and weak electrolytes can be differentiated based on their degree of dissociation. In general terms, the conductivity of an electrolyte solution depends on: (1) the concentration of ions in the solution; (2) the valency of the ion; and (3) the migration velocity or mobility of the ions. For individual electrolyte species at a constant temperature the conductivity is a linear function of the concentration of the electrolyte since the valency and mobility of the ions is constant. Using these known principles to measure the concentration of impurities in an aqueous stream is thus well within the capabilities of the skilled person.

The UV transmittance may also be used as a measurement of the concentration of the impurities in the aqueous ethylene glycol solution. If the aqueous ethylene glycol solution fails to meet certain minimum UV transmittance percentages, then it will be of insufficient quality to qualify as fiber grade and hence the value of it as ethylene glycol will be much reduced. The UV transmittance value in the aqueous glycol solution at breakthrough is as follows:

TABLE I

| Wave Length (nm) | Transmittance %, min |
|---|---|
| 220 | 85 |

When the UV transmittance of the treated aqueous ethylene glycol solution starts to approach these minimum values, this indicates that the capacity of the ion exchange resins of the lean cycle water treatment unit to adsorb impurities from the aqueous ethylene glycol solution has been reached and it needs to be regenerated. Like pH measurement, the UV transmittance is useful in measuring the concentration of non-ionic impurities such as impurities that are especially important to remove like aldehydic impurities. UV transmittance is also a useful measurement because it is a typical product specification for ethylene glycol—an ethylene glycol-containing stream leaving the treatment unit that meets the appropriate UV transmittance level will contribute positively to the final purified ethylene glycol product meeting this specification.

Having been treated in the lean cycle water treatment unit, the treated aqueous stream is preferably sent to the glycol purification section of the plant, where the ethylene glycol is separated from the treated water (and the glycol purified) and the now glycol-free water sent as recycle water to the glycol reactors.

Silver-Based Epoxidation Catalyst

The silver-based epoxidation catalyst includes a support, and at least a catalytically effective amount of silver or a silver-containing compound; also optionally present is a promoting amount of rhenium or a rhenium-containing compound; also optionally present is a promoting amount of one or more alkali metals or alkali-metal-containing compounds. The support employed in this invention may be selected from a large number of solid, refractory supports that may be porous and may provide the preferred pore structure. Alumina is well known to be useful as a catalyst support for the epoxidation of an olefin and is the preferred support.

Regardless of the character of the support used, it is usually shaped into particles, chunks, pieces, pellets, rings, spheres, wagon wheels, cross-partitioned hollow cylinders, and the like, of a size suitable for employment in a fixed-bed epoxidation reactor. The support particles will preferably have equivalent diameters in the range from about 3 mm to about 12 mm, and more preferably in the range from about 5 mm to about 10 mm. (Equivalent diameter is the diameter of a sphere having the same external surface (i.e., neglecting surface within the pores of the particle) to volume ratio as the support particles being employed.) Suitable supports are available from Saint-Gobain Norpro Co., Sud Chemie AG, Noritake Co., CeramTec AG, and Industrie Bitossi S.p.A. Without being limited to the specific compositions and formulations contained therein, further information on support compositions and methods for making supports may be found in U.S. Patent Publication No. 2007/0037991.

In order to produce a catalyst for the oxidation of an olefin to an olefin oxide, a support having the above characteristics is then provided with a catalytically effective amount of silver on its surface. In one embodiment, the catalytic effective amount of silver is from 10% by weight to 45% by weight. The catalyst is prepared by impregnating the support with a silver compound, complex or salt dissolved in a suitable solvent sufficient to cause deposition of a silver-precursor compound onto the support. Preferably, an aqueous silver solution is used.

A promoting amount of a rhenium component, which may be a rhenium-containing compound or a rhenium-containing complex may also be deposited on the support, either prior to, coincidentally with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Other components which may also be deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), rhenium component, and optional additional promoter(s) of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram, preferably from about 0.2 micromoles per gram to about 5 micromoles per gram.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, a rhenium component, an alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.5 to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Further information on catalyst manufacture may be found in the aforementioned U.S. Patent Publication No. 2007/0037991.

EXAMPLES

The invention will now be described in more detail with respect to the following non-limiting examples.

Figure 6:
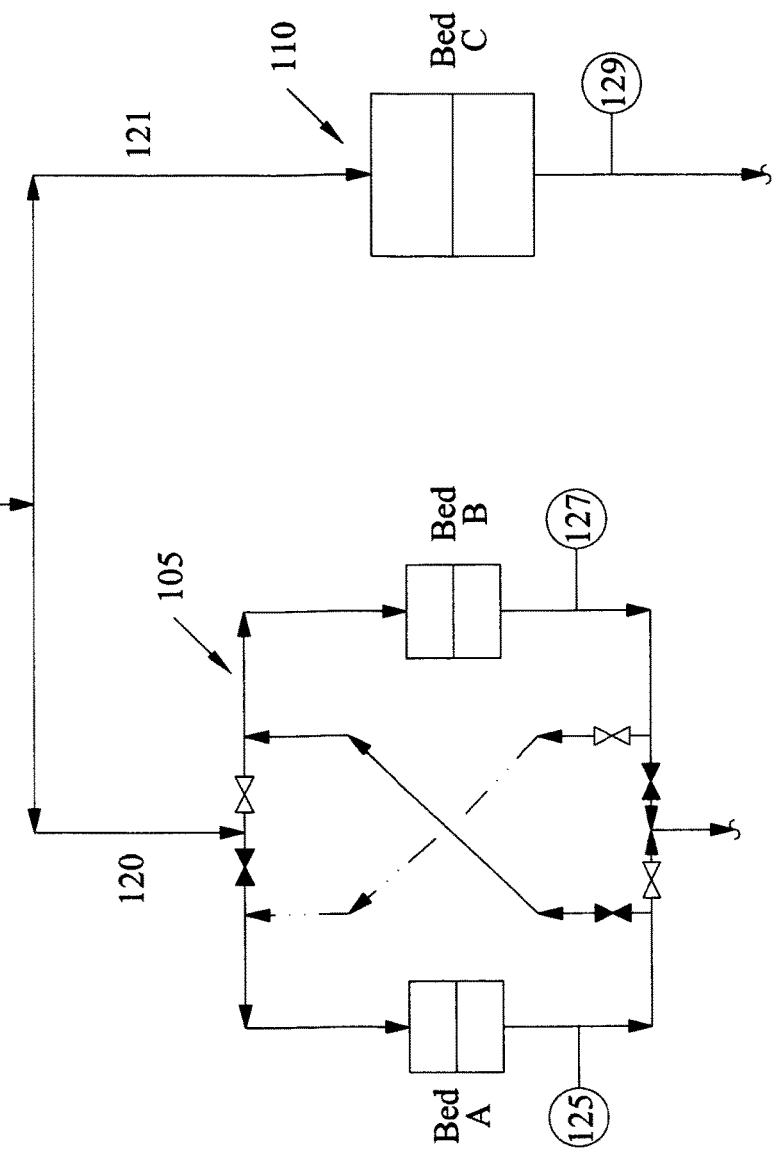
FIG. 6 is a schematic flow sheet showing exemplary methods according to the prior art and according to the present invention for treating an aqueous stream with ion exchange treatment beds.

A treatment unit prepared according to the present invention 105 and a comparative treatment unit prepared according to the prior art 110 are shown in FIG. 6. The treatment unit prepared according to the present invention 105 comprises Bed A and Bed B combined in series, while the prior art comparative treatment unit 110 has only a single Bed C. All three beds A, B, C comprise the same construction, with a first and second chambers. The first chamber containing Tulsion T56 MP cationic resin and the second chamber containing Tuslion A8X MP anionic resin.

To test the relative effectiveness of these treatment units at removing impurities, an aqueous stream 117 taken as a bleed stream (as described above) is obtained from an EO manufacturing facility. The aqueous stream contains the various organic impurities found in the cycle water stream of an EO process such as formic acid, acetic acid, and formaldehydes, among others. The concentration of the impurities in the aqueous bleed stream as measured by conductivity of the stream is shown by the crosses in FIG. 7. As can be seen from FIG. 7, the average concentration of impurities as measured by conductivity in the aqueous bleed stream before being treated is about 102 $\mu$S/cm (indicated by the horizontal line), with values being as high as 144 $\mu$s/cm and low as 60 $\mu$S/cm. The aqueous stream 117 is itself then divided into identical first and second split streams 120, 121 as shown in FIG. 6, with the first split stream 120 being sent to a treatment unit prepared according to the present invention while a second split stream 122 is sent to the comparative treatment unit prepared according to the prior art.

Figure 7:
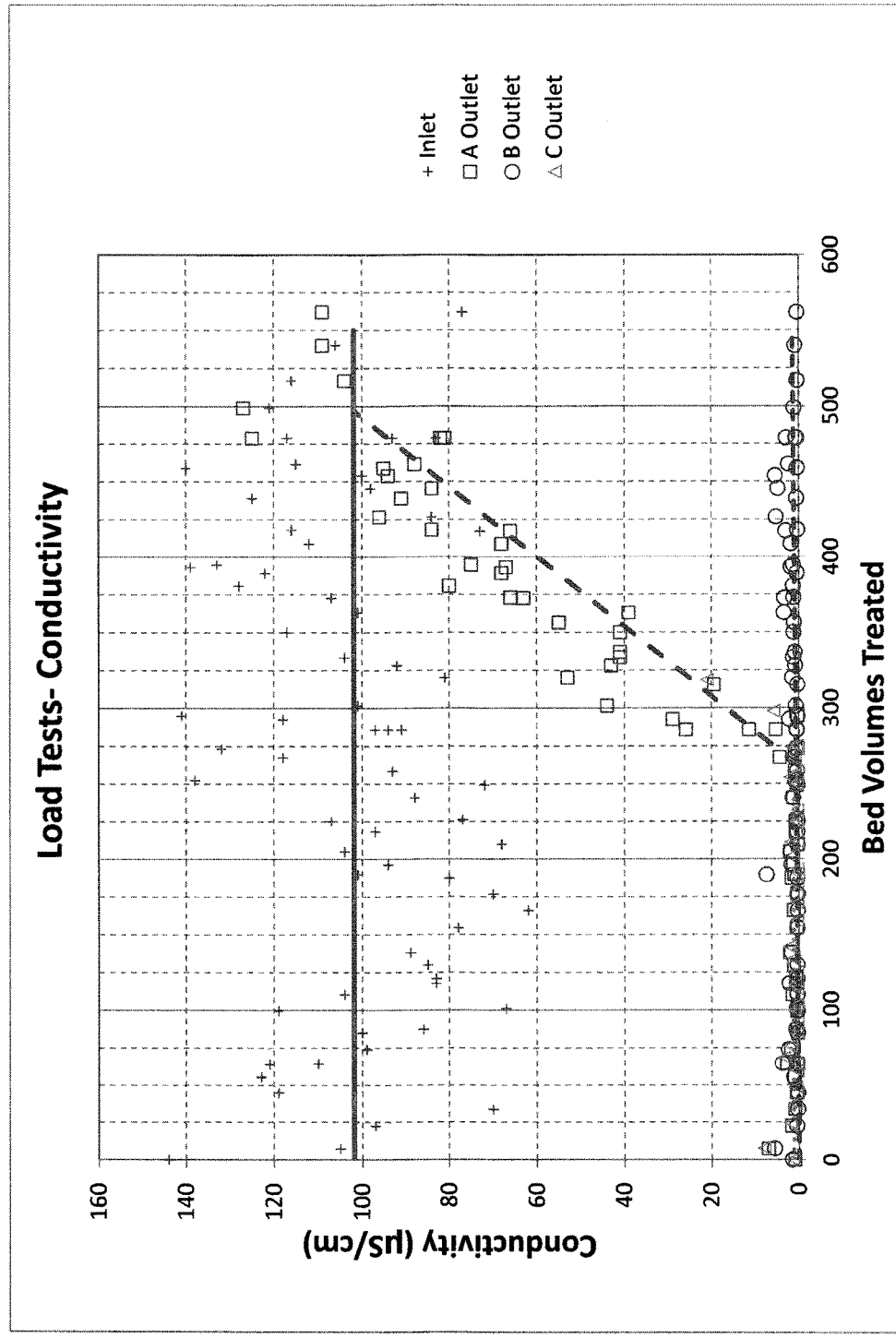
FIG. 7 demonstrates the improvement in service life of an ion exchange treatment unit prepared according to the present invention with plots of the aqueous solution and the treated aqueous solution as a function of time and bed volume of aqueous solution that has been treated by each treatment unit.

The treatment units 105, 110 act to remove impurities from the first and second split streams 120, 121. The concentration of the impurities (as measured by the conductivity of the streams) after impurity absorption upon exiting the beds is measured by analyzers 125, 127, and 129 as shown in FIG. 6. The measured concentration (again as measured by conductivity) is shown in FIG. 7 for Bed A by squares (measured by analyzer 125 upon exiting Bed A), for Bed B by the circles (measured by analyzer 127 upon exiting Bed B) and for Bed C by the triangles (measured by analyzer 129 upon exiting Bed C). So for example, on the 76 hours of operation (at which point in the process approximately 205 bed volumes of the aqueous bleed stream have been processed through each of beds A, B, and C) the aqueous bleed stream supplied from the plant on that day has conductivity of 104 $\mu$s/cm upon being divided into the split streams 120, 121 and input into the treatment units. Impurities are removed from the streams in each treatment unit 105, 110. So upon exiting Bed A the conductivity has fallen from 104 $\mu$s/cm upon input to less than 1 $\mu$s/cm. The stream provided to Bed B has such a low impurity content after treatment in Bed A that Bed B needs to perform little to no impurity or ion absorption, thus saving its absorption capacity for later in the process. Accordingly, the conductivity is little changed after treatment in Bed B, and the split stream exiting Bed B leaves treatment unit 105 with a final measured conductivity of less than 1 $\mu$s/cm.

At the same point in time, the stream exits Bed C and leaves the treatment unit 110 having reduced the conductivity from 104 $\mu$s/cm to 1.4 $\mu$s/cm.

After approximately 106 hours (at which the bed volume treated is approximately 285-300), the situation has changed considerably. The stream exits bed A with a conductivity of approximately 5 $\mu$s/cm, indicating that bed A is now only partially effective at removing impurities from the stream because its capacity has been reduced as it nears closer to exhaustion. However, Bed B acts to reduce the conductivity of the stream exiting Bed B and the treatment unit 105 to a value of less than 1, meaning that the treatment unit of the present invention has not suffered any loss of effectiveness at removing impurities from the first split stream 120.

Bed C and the treatment unit of the prior art performs similarly. The conductivity is also approximately 5 $\mu$s/cm at this same point. But, as also can be seen in FIG. 7, Bed C has clearly reached exhaustion after 120 hours of operation (at which point 320 bed volumes have been treated in Bed C), the conductivity of the treated streams passing through Bed C start to rise dramatically—the conductivity climbs and crosses the conductivity value of 20. At this point, the Bed C is no longer effectively removing impurities and the treatment unit prepared according to the prior art now has to be taken off-line to be regenerated.

The treatment unit prepared according to the present invention, however, continues to operate effectively removing impurities. At longer time periods of operations Bed A's active sites have been significantly saturated and Bed A is now less ineffective at removing impurities as shown by the high conductivity of the aqueous streams leaving Bed A (see FIG. 7). For example, at approximately 148 hours of operation (at which point 400 bed volumes have been treated in Bed A), the stream input into Bed A has a relatively high impurity load as shown by the measured conductivity of almost 133. Bed A reduces this significantly, but nonetheless the measured conductivity of the stream exiting Bed A is still an unacceptably high 75. The conductivity values of the stream leaving Bed A increases in a roughly linear trend over the next several days as shown by the fitted trend (dashed) line. However, Bed B has sufficient capacity remaining to absorb the impurities Bed A was unable to and thus, consistently reduces the conductivity value of the resulting stream to below 5 $\mu$S/cm, which as described above has been discovered in the present invention to be a critical parameter in ensuring efficient plant operation and product quality. Bed A is able to reduce impurities so that the measured conductivity of the stream leaving Bed A remains below 5 $\mu$S/cm for the duration of the experimental run—until the example was terminated just short of 580 bed volumes treated.

As a result, it is not necessary to take the treatment unit prepared according to the present invention off-line for regeneration until long after the prior art unit has already been taken off-line. The treatment unit prepared according to the prior art must be taken-off line after approximately 120 hours of operation (at which point 320 bed volumes have been treated). By contrast, the treatment unit prepared according to the present invention was still reducing stream impurities according to design even after 580 bed volumes had been treated. Thus, the treatment unit prepared according to the present time can go for longer between ion exchange bed regenerations. As mentioned above, increasing the time between regenerations greatly increases the efficiency of the process while simultaneously reducing the cost of operating it.

It will be appreciated by those skilled in the art that changes could be made to the embodiments described above without departing from the broad inventive concept thereof. It is understood therefore that this invention is not limited to the particular embodiments disclosed, but it is intended to cover modifications within the spirit and scope of the present invention as defined by the appended claims.

What we claim is:

1. A method for removing impurities from a lean cycle water effluent of an ethylene oxide manufacturing plant, the method comprising:

providing an aqueous stream containing ethylene glycol and impurities;

introducing the aqueous stream into a first ion exchange treatment bed to reduce the content of the impurities;

determining whether an outlet of the first ion exchange treatment bed has a conductivity greater than about 5 µS/cm;

upon determining that the outlet of the first ion exchange treatment bed has a conductivity greater than about 5 µS/cm, introducing the outlet of the first ion exchange treatment bed into a second ion exchange treatment bed, while keeping the first ion exchange treatment bed on-line and working simultaneously with the second ion exchange treatment bed; and upon determining that the outlet of the first ion exchange treatment bed has a conductivity greater than about 20 to about 100 µS/cm, redirecting the introduction of the aqueous stream to the second ion exchange treatment bed and regenerating the first ion exchange bed.

2. The method according to claim 1, wherein the impurities are selected from long chain esters, formaldehyde, acetaldehyde, glycolaldehyde and their associated acids and ions, and mixtures thereof.

3. The method according to claim 1, wherein the aqueous stream comprises 0.2 to 20 wt % ethylene glycol.

4. The method according to claim 1, wherein the process further comprises the step of passing the aqueous stream to a glycol purification section.

5. The method according to claim 1, wherein the temperature in the first ion exchange treatment bed is about 30° C. to about 50° C.

6. The method according to claim 1, wherein the regenerating step comprises contacting the first ion exchange bed with a regenerant selected from potassium hydroxide, sodium hydroxide, hydrochloric acid, and sulfuric acid.

7. The method according to claim 1, wherein the first and second ion exchange treatment beds contain resins selected from the group consisting of cationic exchange resins, anionic exchange resins, and mixtures thereof.

8. The method according to claim 1, further comprising initiating an epoxidation reaction by reacting a feed gas composition containing ethylene and oxygen in the presence of an epoxidation catalyst comprising a promoting amount of rhenium.

* * * * *